United States Patent [19]

Mongeon

[11] Patent Number: 4,819,334
[45] Date of Patent: Apr. 11, 1989

[54] ORBITAL SAW DEVICE

[75] Inventor: Douglas R. Mongeon, Orange, Calif.

[73] Assignee: Minnesota Mining and manufacturing Company, St. Paul, Minn.

[21] Appl. No.: 492,042

[22] Filed: May 6, 1983

[51] Int. Cl.⁴ .............................................. B23D 49/04
[52] U.S. Cl. ...................................... 30/393; 128/317; 83/835
[58] Field of Search ......................... 30/392, 393, 394; 128/317; 76/25 R; 83/835, 697, 698

[56] References Cited

U.S. PATENT DOCUMENTS

| | | | |
|---|---|---|---|
| 1,326,166 | 12/1919 | Backus | 128/317 X |
| 2,137,893 | 11/1938 | Elder | 143/68 |
| 2,455,655 | 12/1948 | Carroll | 128/317 |
| 3,023,645 | 3/1962 | Craven et al. | 76/25 R |
| 3,554,197 | 1/1971 | Dobbie | 128/317 |
| 3,572,409 | 3/1971 | Hoffman | 143/68 |
| 3,823,473 | 7/1974 | Hoffman | 30/338 |
| 3,977,289 | 8/1976 | Tuke | 83/835 |
| 4,106,181 | 8/1978 | Mattchen | 29/450 |
| 4,386,609 | 6/1983 | Mongeon | 128/317 |

FOREIGN PATENT DOCUMENTS 453529  12/1927  Fed. Rep. of Germany ........ 30/392

Primary Examiner—Frank T. Yost
Assistant Examiner—Willmon Fridie, Jr.
Attorney, Agent, or Firm—Donald M. Sell; Robert W. Hoke, II

[57] ABSTRACT

An orbital saw for use in orthopedic applications such as cutting bones including a one-piece, externally mounted saw blade that can be quickly and easily replaced by unlocking a pair of blade clamps. The saw can be battery operated. The battery is keyed and locked with a hand grip by a release lever to form a handle. The battery can be unlocked and replaced when it becomes run down.

1 Claim, 4 Drawing Sheets

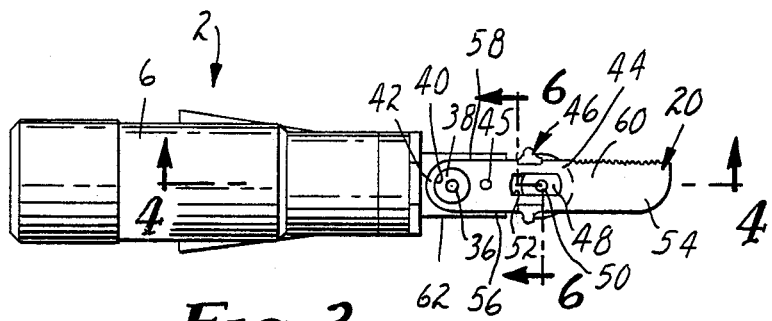
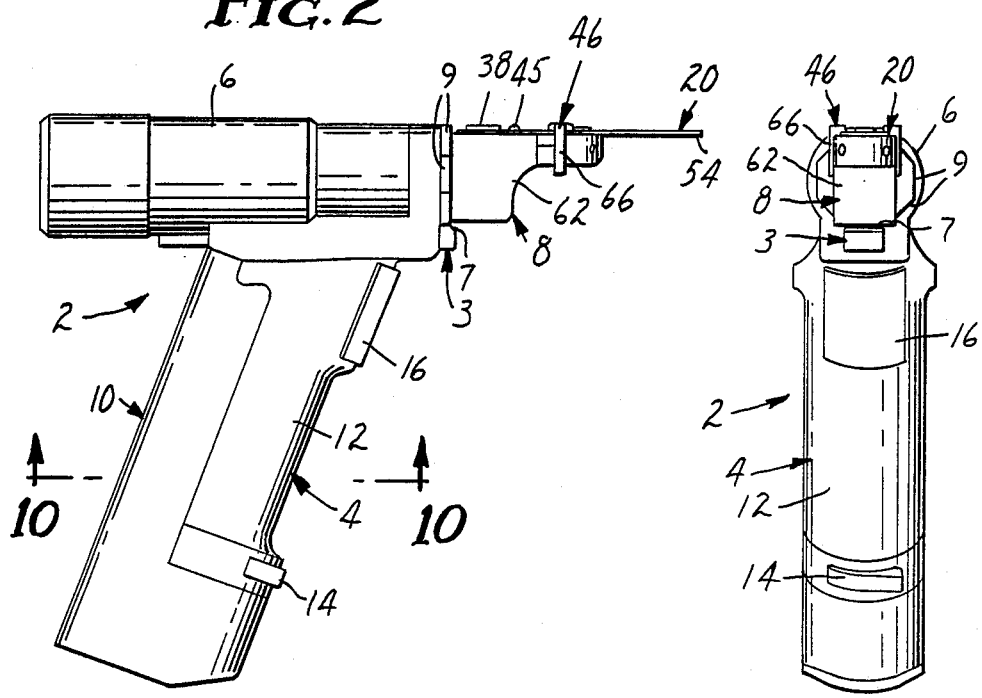
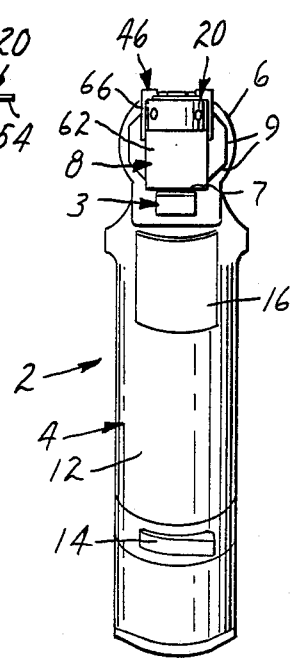

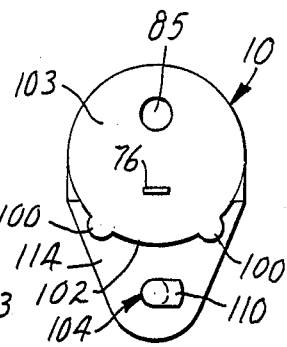
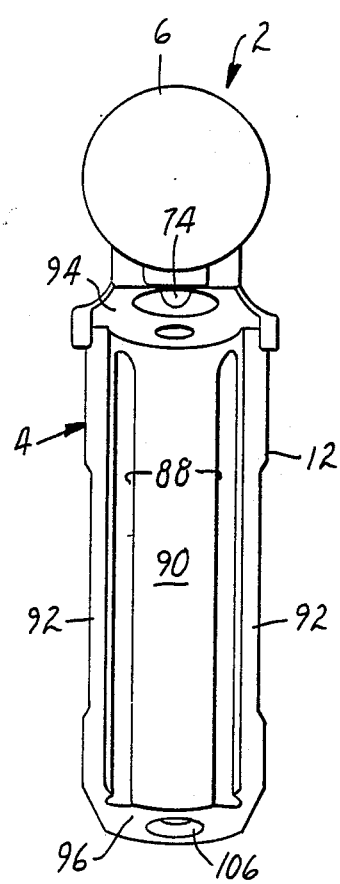
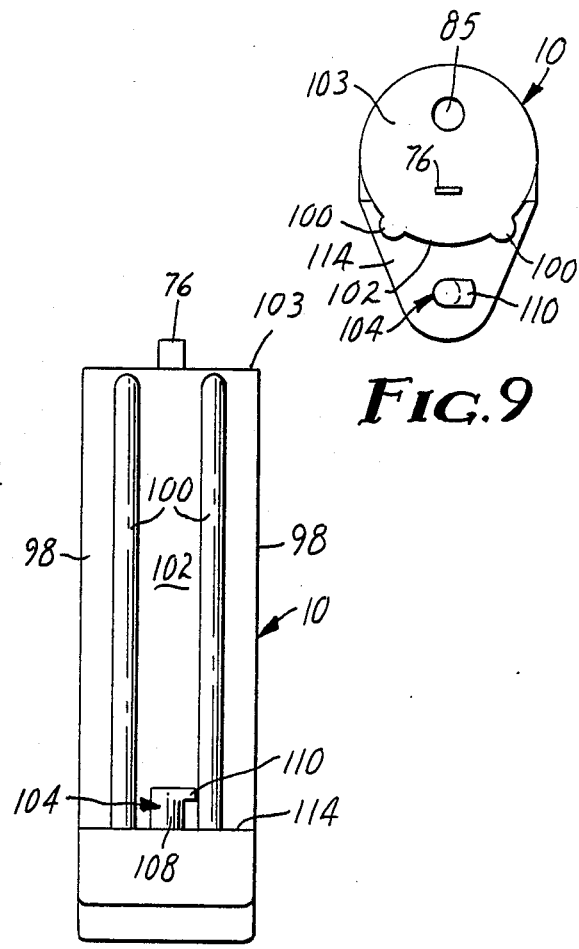
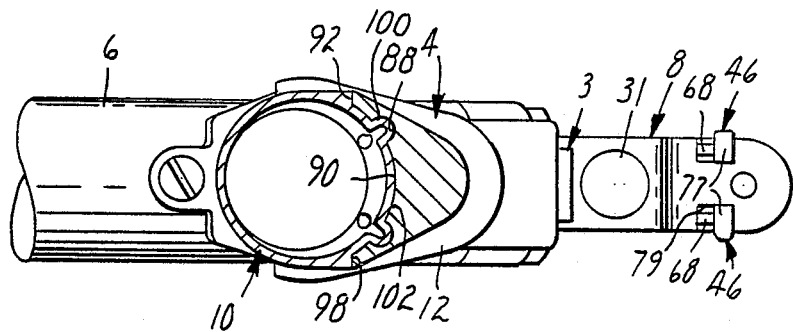

ORBITAL SAW DEVICE

BACKGROUND

The present invention relates to saws. More particularly, it relates to medical and orthopedic saws in which the blades move in an orbital fashion at the work end.

Medical and orthopedic saws are generally hand held. Some are manually operated. Some are electrically or pneumatically operated. It is known to use such saws to remove fracture casts, to saw bones and to perform other medical and orthopedic procedures by using different saw blades.

U.S. Pat. No. 3,905,105 describes such an orthopedic bone saw. It has a blade carrier and a separate blade. The blade carrier includes a first end portion and an intermediate portion housed in a casing and a second end portion projecting from the casing. The first end portion is coupled with an eccentric, rotary drive spindle. The intermediate portion is constrained by the casing for longitudinal translation and pivotal movement. A blade is connected with the second end portion. When the saw is energized, each point along the free end of the blade moves in an elliptical path.

The blade carrier is a permanent part of the saw. In use, considerable pressure may be applied to the bearing points between the casing and the carrier resulting in wear and eventual failure of the blade carrier. To afford a longer life, it is believed the blade carrier disclosed in U.S. Pat. No. 3,905,105 must be relatively heavy and bulky in construction and well lubricated to reduce wear. Also, it should be protected from foreign materials, as recited in the patent, to extend its useful life. This is said to be accomplished by piston-like blocks in the area where the blade carrier emerges from the casing. As disclosed, the portions of the blade carrier where wear may occur are housed within the hollow casing. This additional casing and relatively heavy blade carrier add weight to the saw. This is both expensive and burdensome in a hand-held device.

SUMMARY OF THE INVENTION

The saw of the present invention overcomes many of the disadvantages of the prior medical and orthopedic saws in the manner in which the saw blade in constructed and attached to the saw. Further, the manner in which the saw blade can be released from the saw and the manner in which the power source can be releasably secured to the handle of the saw represent significant improvements in the art.

According to the invention, there is provided a handheld electic or air-powered saw for use in orthopedic applications such as bone cutting. The saw includes a housing having a flat outer surface. A rotary drive member extends through the flat surface and has an eccentric thereon adjacent the flat surface. A bearing is mounted on the eccentric. A first end portion of a saw blade rides on the bearing adjacent the flat surface. An intermediate portion of the saw blade is pivotally mounted on a yoke on the housing and adjacent the flat surface and is constrained thereon by two blade clamps whereby the intermediate portion of the saw blade may reciprocate as the first end is eccentrically driven to drive a second end portion of the saw blade including a plurality of cutting edges in an orbital fashion. The blade clamps may be locked adjacent the saw blade to hold the saw blade adjacent the flat surface on the housing, or they may be unlocked to allow removal or replacement of the saw blade.

The portions of the saw most susceptible to wear, i.e., the end portion of the blade attached to the eccentric and the pivotally mounted intermediate portion are restored to their original condition each time the blade is replaced. The saw blade may be quickly and easily replaced. Furthermore, the blade may be inexpensively stamped out. The saw can be battery operated. The battery fits conveniently within a handle. The handle is formed into a shape comfortable for handling. The battery is keyed and locked with a hand grip by a release lever to form an integral part of the handle when the saw is used. A stud on the battery fits within a recess within the release lever and is locked therein when the release lever is rotated to the locked position. Hence, the battery may be quickly and easily replaced.

BRIEF DESCRIPTION OF THE DRAWINGS

Other advantages of the invention will become apparent from the following drawings where like numerals refer to like parts, the accompanying description and the appended claims.

FIG. 1 is side elevational view of a hand held, battery operated saw including a saw blade capable of moving in an elliptical path.

FIG. 2 is a top view of the saw of FIG. 1.

FIG. 3 is a front elevational view of the saw of FIG. 1.

FIG. 7 is a rear elevational view of the saw of FIG. 1 with a battery pack removed.

FIG. 8 is a front elevational view of the battery pack with the saw of FIG. 1 which was removed from FIG. 7.

FIG. 9 is a top view of the battery pack of FIG. 8.

FIG. 10 is a sectional view taken along 10—10 of FIG. 1.

DETAILED DESCRIPTION

Figure 4:
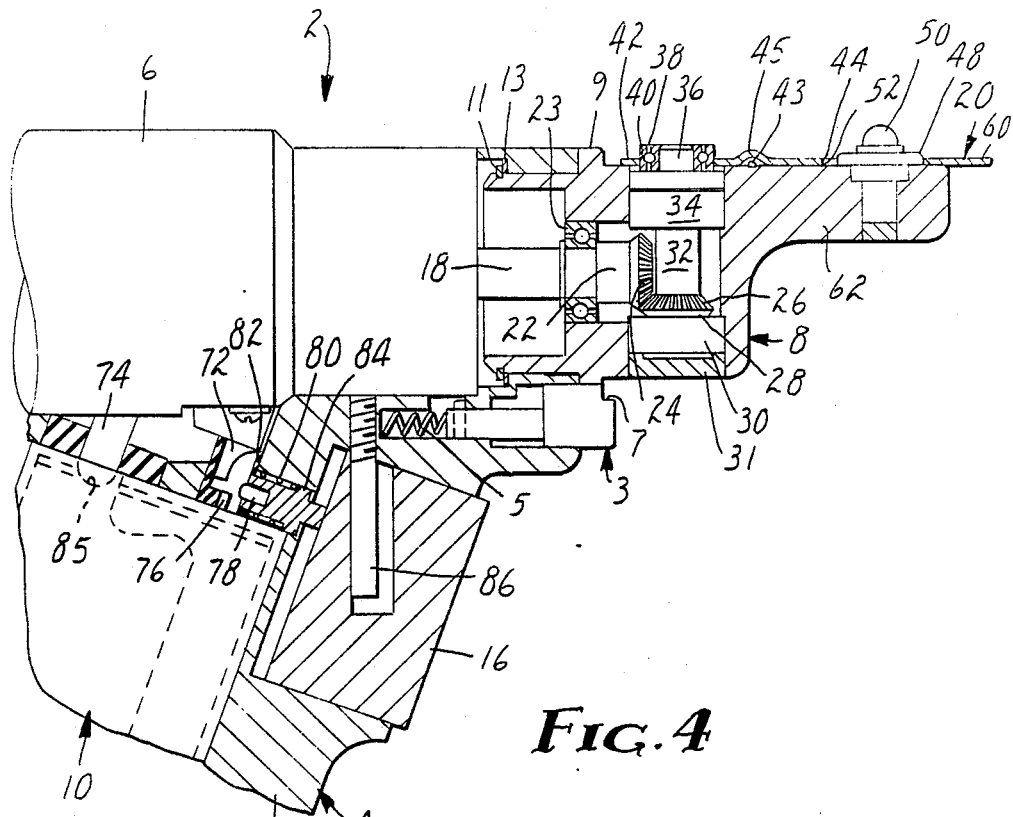
FIG. 4 is an enlarged fragmentary sectional view taken along line 4—4 of FIG. 2.

Referring to the figures wherein like reference characters designate like parts throughout the several views and more particularly to FIG. 1 and FIG. 4, a handheld, battery operated saw 2 is shown. The saw is generally comprised of a handle portion 4, a motor 6 and a saw blade driving mechanism 8. The handle portion 4 includes a battery pack 10 releasably attached to a grip 12 by a release lever 14. Upon depression of a trigger 16, the battery pack 10 energizes the motor 6 to rotate the motor shaft 18 in a manner to be explained. The motor shaft 18, in turn, drives elongate integral the saw blade 20.

The orientation of the saw blade 20 relative to the handle portion 4 may be changed by depression of a plunger 3. Plunger 3 is biased in the position shown by compression spring 5. Upon depression, a notch 7 within the plunger 3 is aligned with ridges 9 on a saw housing 62 to allow the mechanism 8 to rotate around the longitudinal axis of the motor shaft 18. This is accomplished by a "Spirolox" lock 11 sliding on a shear ring 13. "Spirolox" lock 11 is a dished, resilient take-up ring available from Ramsey Corporation, P.O. Box 513, St. Louis, Mo. 63166, a subsidiary of TRW, Inc., as part number MS-100. When the desired orientation is reached, the plunger 3 is released, and one of the ridges 9 is again locked against further movement by the plunger 3.

Referring particularly to FIG. 4, the motor shaft 18 has a beveled gear 22 supported on the output end of the motor shaft 18. The motor shaft 18 is supported by a bearing 23. The teeth 24 of the beveled gear 22 mesh with teeth 26 of a beveled gear 28. The beveled gear 28 is supported by a bearing 30. The bearing 30 is positioned on one end portion of a drive shaft 32 and covered by a cover plate 31. The distal end portion of the drive shaft 32 is supported by a bearing 34. The distal end portion of the drive shaft 32 extends through the bearing 34, and includes an eccentric plate 36. A bearing 38 is pressed on the eccentric plate 36 and is adapted to eccentrically drive the saw blade 20 in a manner to be explained.

Referring now to FIG. 2 and FIG. 4, the saw blade 20 is shown riding on the bearing 38. The saw blade 20 has a cylindrical drive surface defining a receiving aperture 40 within a proximal end portion 42. The proximal end portion 42 of the saw blade 20 fits over the bearing 38 to frictionally fit the bearing 38 within the aperture 40. A protuberance 43 on the saw housing 62 and a curved poriton 45 of the saw blade 20 preferably prevent the saw blade 20 from being mounted upside down on the bearing 38.

An intermediate portion 44 of the saw blade 20 is constrained by blade clamps 46 and a guide yoke 48. The yoke 48 is pivotally mounted on a pin 50. The intermediate portion 44 of the saw blade 20 has a receiving slot 52 therein, partially defined by facing guide surfaces allowing the intermediate portion 44 to move longitudinally on the yoke 50. The slot 52 has a longitudinal length greater than the longitudinal length of the yoke 48 to allow the longitudinal motion described.

When the proximal end 42 of the saw blade 20 is eccentrically driven by the bearing 38, the intermediate portion 44 of the saw blade 20 is longitudinally driven on the pivotally mounted yoke 48. This results in an elliptical motion at a distal or free end portion 54 of the saw blade 20.

Lateral motion of the intermediate portion 44 of the saw blade 20 is prevented by the yoke 48. Blade clamps 46 are juxtaposed edges 56 and 58 and a top surface 60 of the saw blade 20. The bottom surface (not shown) of the saw blade 20 rides on the saw housing 62.

Figure 6:
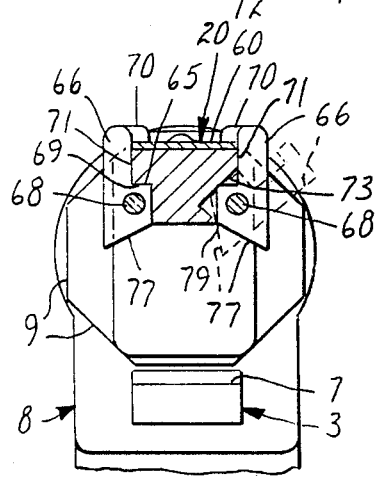
FIG. 6 is an enlarged sectional view taken along line 6—6 of FIG. 2.
Figure 5:
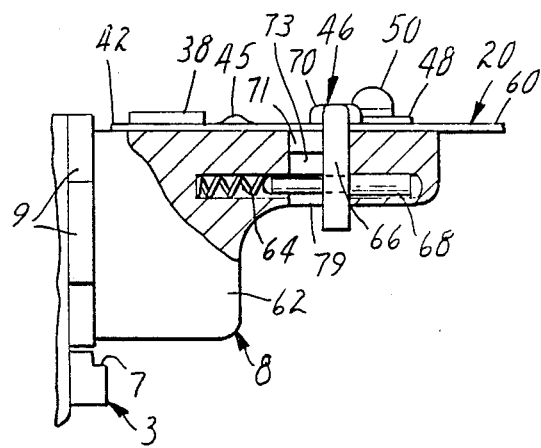
FIG. 5 is a partial sectional view of the saw of FIG. 4 showing the structure for attaching the saw blade.

FIGS. 5 and 6 illustrate the workings of the blade clamps 46. In the forward position, shown in FIG. 5, the blade clamps 46 are locked in an upright position by surfaces 65 of the blade clamps 46 contacting surfaces 69 of the saw housing 62. When the blade clamps 46 are slid rearwardly against the pressure of springs 64, lever arms 66 of the blade clamps 46 are allowed to pivot downwardly around the longitudinal axes of supporting slides 68 as shown in phantom line in FIG. 6. This is made possible by beveled portions 73 of the saw housing 62. The lever arms 66 pivot through an arc of approximately forty-five degrees until bottom surfaces 77 of the lever arms 66 contact edges 79 of the saw housing 62.

The downward pivoting of the blade clamps 46 raises ridges 70 of the blade clamps 46 away from the top surface 60 of saw blade 20. As the ridges 70 are raised and pivoted away, the saw blade 20 is released from the blade clamps 46; the saw blade 20 may then be removed from the bearing 38 and the yoke 48.

The manner in which the battery pack 10 powers the motor 6 will next be explained. Referring to FIG. 4, the motor 6 is shown to include a positive terminal 72 and a negative terminal 74. With the battery pack 10 in place, the negative terminal 74 mates with a negative terminal 85 of the battery pack, and the positive terminal 72 of the motor 6 is brought in close proximity with a positive terminal 76 of the battery pack 10.

Upon depression of the trigger 16, an electrical contact 78 bridges the gap between the positive terminal 72 of the motor 6 and the positive terminal 76 of the battery pack 10, resulting in energization of the motor 6. When the trigger 16 is not depressed, the contact 78 is biased away from the positive terminals 72 and 76 by a compression spring 80. The spring 80 is compressed between a stop plate 82 and a contact sleeve 84. The contact 78 is press fit within the contact sleeve 84.

The trigger 16 is prevented from disengaging from the grip 12 by a trigger pin 86. The trigger pin 86 conveniently screws into the grip 12. The trigger 16, upon depression, moves the contact sleeve 84 against the compression spring 80 to interconnect the positive terminals 72 and 76 with the contact 78 as already described.

The manner in which the battery pack 10 is adapted to and locks with the grip 12 will next be described in conjunction with FIGS. 7-13. Referring first to FIG. 7, there is shown a rear elevational view of the saw 2 of FIG. 1 with the battery pack 10 removed. The grip 12 includes two longitudinal slots 88 within a curved surface 90. The outside edges of the curved surface 90 are bounded by surfaces 92. Above the curved surface 90 is a surface 94.

As shown in FIGS. 8 and 9, the battery pack 10 is provided with mating surfaces. Surfaces 98 mate with the surfaces 92; ridges 100 mates with the slots 88; a curved surface 102 mates with the curved surface 90.

Figure 12:
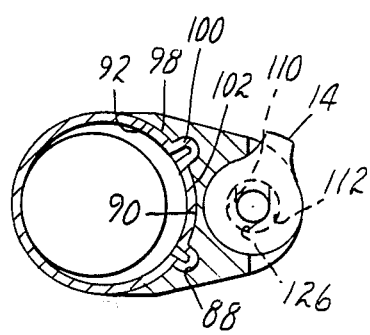
FIG. 12 is a sectional view taken along line 12—12 of FIG. 11
Figure 13:
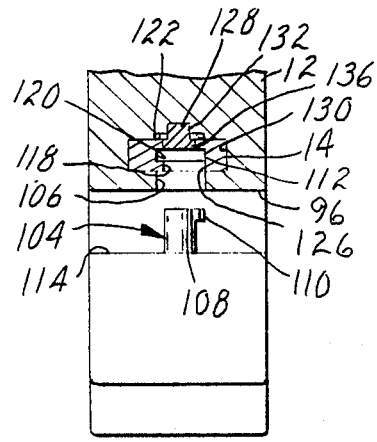
FIG. 13 is a fragmentary sectional view taken along line 13—13 of FIG. 11 with the battery pack shown in elevation just prior to attachment.

The battery pack 10 is slid onto the grip 12 from below until a top surface 103 of the battery pack 10 abuts the surface 94 of the grip 12. In this way, the positive terminals 72 and 76 and the negative terminals 74 and 85, respectively, are properly aligned and interconnected as described earlier. As the battery pack 10 is slid into position, a stud 104 of the battery pack 10 enters an aperture 106 in the grip 12 as shown in FIG. 13. Once in position, as shown in FIG. 11, the stud 104 may be locked within a cavity 112 within the release lever 14 as shown in FIG. 12.

Figure 11:
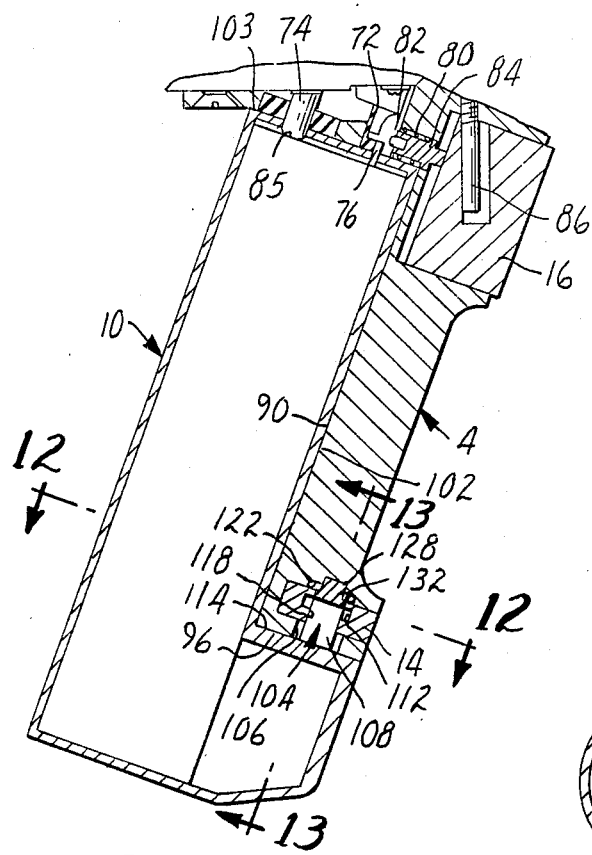
FIG. 11 is an enlarged fragmentary sectional view of a handle portion of the saw of FIG. 1.

FIG. 13 is a sectional view taken along the line 13—13 of FIG. 11 with the battery pack 10 shown in elevation and just prior to insertion into the aperture 106. The stud 104 is shown to comprise a cyclindrical portion 108 and an arcuate section 110. A top view of the stud 104 showing the shape of the arcuate section 110 may be seen in FIG. 9. The stud 104 is inserted into and through the aperture 106 until a surface 96 of the grip 12 is contacted by a surface 114 of the battery pack 10. The positioning of the stud 104 within the aperture 106 of the grip 12 and the cavity 112 of the release lever 14 when the battery pack 10 is fully slid into place on the grip 12 may best be seen in FIG. 11.

Referring to FIGS. 11 and 13, the cavity 112 within the release lever 14 comprises a bore 118 reamed out at a portion 120 to accommodate the arcuate section 110 of the stud 104. As seen in FIG. 13, the bore 118 of the cavity 112 includes a cutout 126 to allow the passage of the arcuate section 110 through the bore 118 and into the reamed out portion 120. The cutout 126 is shown in phantom line in FIG. 12. The release lever 14 is shown in the locked position with the arcuate section 110 of the stud 104 locked within the reamed out portion 120 of the cavity 112 within the release lever 14. The lever 14 may preferably be biased in the locked position by a torsion spring 122. One end, not shown, of the spring 122 may be embedded within the grip 12 and the other end, not shown, embedded in the lever 14 to hold the release lever 14 in the locked position as well known in the art. To release the stud 104, the release lever 14 must be rotated counter-clockwise until the cutout 126 and the arcuate section 110 are vertically aligned. Upon alignment, the arcuate section 110 may be retracted from the reamed out portion 120 of the cavity 112 through the cutout 126 in the bore 118 and out the aperture 106 in the grip 12.

The release lever 14 is held within the grip 12 by a hat-shaped release keeper 128 shown in FIGS. 11 and 13. In assembly, the release lever 14 is first placed a within a cavity 130 of the grip 12. Next, the release keeper 128 is inserted through the aperture 106 and the cavity 112 within the release lever 14 and lodged partially within the upper portion of the bore 118 and partially within the grip 12. A portion 132 of the release keeper 128 fits snugly within an unnumbered recess of the grip 12. A portion 136 of the release keeper 128 fits within the upper end of the bore 118 within the lever 14 to prevent the lever 14 from falling out of the cavity 130 of the grip 12 while still permitting pivotal movement of the lever 14 to alternatively lock and unlock the stud 104 as described earlier.

With the stud 104 in place as shown in FIG. 11 and securely locked against disengagement by turning the release lever to the position shown in FIG. 12, saw 2 may be energized by depressing the trigger 16 as described earlier. Once energized, the saw 2 may be used with a variety of saw blades 20 to perform medical and orthopedic tasks. For example, it may be used to saw bones. Each time the saw blade 20 is replaced, the saw 2 is restored to nearly its original condition by replacing the elements most prone to wear, i.e., the proximal end portion 42 and the intermediate portion 44 of the saw blade 20. The blade 20 may be quickly and easily replaced by releasing the blade clamps 46 in the manner already described. When the battery pack 10 runs down, it, too, may be replaced in the manner described. The saw 2 is compact and hand-held. It may be easily used to perform many medical and orthopedic tasks. When in use, the saw blade 20 and the battery pack 10 are solidly affixed. Both may be easily and quickly released when circumstances warrant to facilitate operating procedures.

The versatility of the saw 2 is greatly enhanced by the rotatability of the saw blade 20 relative to handle portion 4 as described earlier. Without this ability, the physician would have to adjust his grip to reach certain areas. With this ability, the saw blade 2, rather than the physician's grip is adjusted to meet the need. This rotatable feature is made possible by the construction and operation of saw blade driving mechanism 8 as described earlier.

Various modifications and changes may be made by one skilled in the art and without departing from the spirit of the invention as expressed in the accompanying claims. Hence, all matter shown and described is to be interpreted as illustrative and not in a limiting sense.

What is claimed is:

1. An elongate, integral saw blade having opposite major surfaces and a peripheral edge surface, said blade comprising:
   a. a first end portion having a cylindrical drive surface between said major surfaces defining a through drive aperture adapted to receive a drive bearing;
   b. an intermediate portion extending from said first end portion and having a guide aperture between said major surfaces adapted to engage a guide, said guide aperture being partially defined by facing guide surfaces located between said major surfaces and longitudinally aligned with said blade;
   c. a second end portion extending from said intermediate portion opposite said first end portion and having a plurality of cutting edges along said peripheral edge surface; and
   d. means between said drive aperture and said guide aperture for preventing reception of said drive bearing and engagment of said guide from one of said opposite major surfaces.

* * * * *